US007688984B2

(12) United States Patent
De Callafon

(10) Patent No.: US 7,688,984 B2
(45) Date of Patent: Mar. 30, 2010

(54) ACTIVE NOISE CONTROL METHOD AND APPARATUS INCLUDING FEEDFORWARD AND FEEDBACK CONTROLLERS

(75) Inventor: Raymond De Callafon, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 678 days.

(21) Appl. No.: 10/579,520

(22) PCT Filed: Nov. 24, 2004

(86) PCT No.: PCT/US2004/039532

§ 371 (c)(1),
(2), (4) Date: May 15, 2006

(87) PCT Pub. No.: WO2005/053586

PCT Pub. Date: Jun. 16, 2005

(65) Prior Publication Data

US 2007/0086598 A1 Apr. 19, 2007

Related U.S. Application Data

(60) Provisional application No. 60/525,568, filed on Nov. 26, 2003.

(51) Int. Cl.
*A61F 11/06* (2006.01)
*G10K 11/16* (2006.01)
*H03B 29/00* (2006.01)

(52) U.S. Cl. .................. 381/71.11; 381/71.12; 708/322

(58) Field of Classification Search ..... 381/71.1–71.14; 708/322
See application file for complete search history.

(56) References Cited

U.S. PATENT DOCUMENTS 5,278,780 A 1/1994 Eguchi
5,535,283 A 7/1996 Saruta et al.
6,208,739 B1 3/2001 Venugopal et al.

FOREIGN PATENT DOCUMENTS

EP 0 654 901 A1 5/1995
EP 0 814 456 A2 12/1997

OTHER PUBLICATIONS

R.A. de Callafon, J. Zeng, C.E. Kinney, "Active Noise Control for the Forced-Air Cooling System in a Data Projector", Preprint submitted to Elsevier Science, Jul. 29, 2004, pp. 1-18.

(Continued)

*Primary Examiner*—Xu Mei
(74) *Attorney, Agent, or Firm*—Greer, Burns & Crain, Ltd.

(57) ABSTRACT

An active noise control apparatus for reducing noise from a noise source includes a microphone for detecting noise produced by the noise source, and a generalized finite impulse response (FIR) filter for receiving noise signals of the detected noise from the microphone and generating control signals for reducing the noise from the noise source. A speaker produces sound based on the control signals from the generalized FIR filter for substantially canceling the noise from the noise source.

12 Claims, 5 Drawing Sheets

OTHER PUBLICATIONS

E. Esmailzadeh, A. Alasty, A.R. Ohadi, "Hybrid Active Noise Control of a One-Dimensional Acoustic Duct," ASME Journal of Vibration and Acoustics, vol. 124, 2002, pp. 10-18.

C.R. Fuller, A.H. Von Flotow, "Active Control of Sound and Vibration," IEEE Control Systems Magazine, vol. 15, No. 6, Dec. 1995, pp. 9-19.

J.S. Hu, J.F. Lin, "Feedforward Active Noise Controller Design in Ducts Without Independent Noise Source Measurements," IEEE Transactions on Control System Technology, vol. 8, No. 3, 2000, pp. 443-455.

C.E. Kinney, R.A. de Callafon, "Periodic Disturbance Rejection with an Internal Model-Based $H_2$ Optimal Controller".

K.K. Shyu, C.Y. Chang, "Modified FIR Filter with Phase Compensation Technique to Feedforward Active Noise Controller Design," IEEE Transactions on Industrial Electronics, vol. 47, No. 2, Apr. 2000, pp. 444-453.

J. Zeng, R.A. de Callafon, "Feedforward Noise Cancellation in an Airduct using Generalized FIR Filter Estimation", Proceedings on Decision and Control, Maui, Hawaii, Dec. 2003, pp. 6392-97.

R.J. Bernhard, "Strategies for Active and Passive Noise Control," Canadian Acoustics, vol. 28, No. 3, 2000, pp. 8-9.

Peter S.C. Heuberger, Paul M.J. Van den Hof, "A Generalized Orthonormal Basis for Linear Dynamical Systems", IEEE Transactions on Automatic Control, vol. 40, No. 3, Mar. 1995, pp. 451-465.

FIG. 5
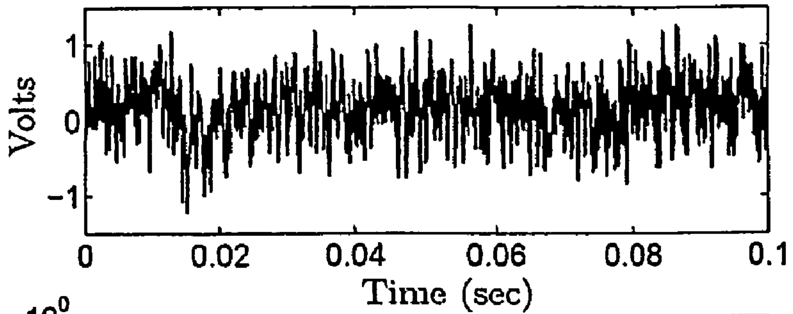
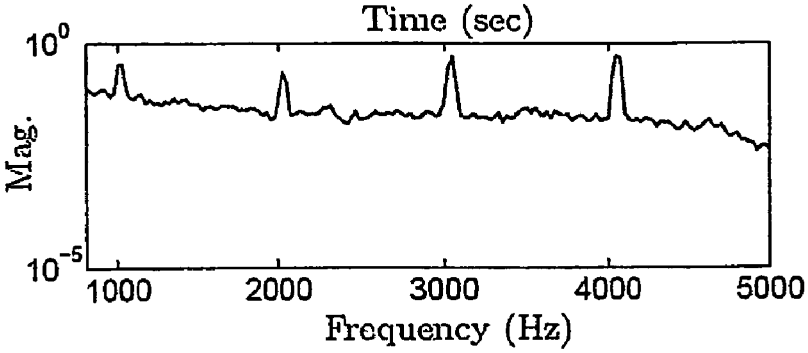
FIG. 6
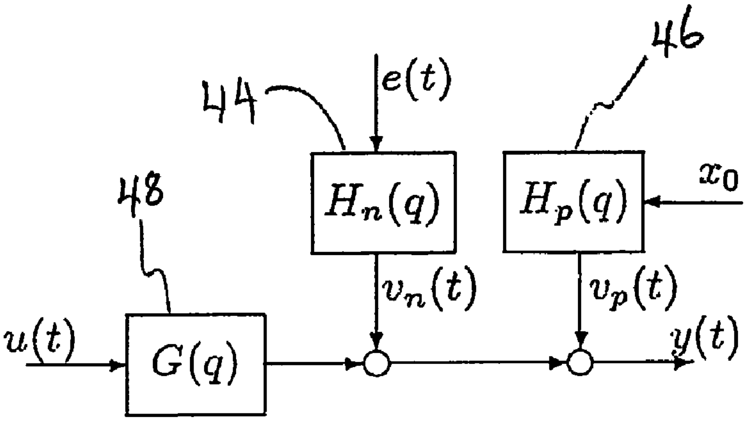
FIG. 7

ACTIVE NOISE CONTROL METHOD AND APPARATUS INCLUDING FEEDFORWARD AND FEEDBACK CONTROLLERS

PRIORITY CLAIM

Applicants claim priority benefits under 35 U.S.C. § 119 on the basis of Patent Application No. 60/525,568, filed Nov. 26, 2003.

TECHNICAL FIELD

Fields of the invention include noise cancellation. The invention concerns other more particular fields, including, but not limited to, active noise control using a feedforward or a feedback controller.

BACKGROUND ART

Sound is an undesired result of many desirable functions. The control of undesired sound is important in any number of devices. Without some control of sound emitted, for example, by modern devices, many modern environments would be largely intolerable to people. Be it the household, the office, the inside of a vehicle, a manufacturing plant, everyday devices produce noise that must be controlled.

One aspect of noise reduction is to make devices and systems that inherently produce less noise. For example, in computers a solid state memory produces little to no noise when compared to a disk drive. Similarly, an LCD display produces little to no noise when compared to a CRT.

In many instances, however, noise creating features cannot be eliminated. Examples of noise producing devices include motors and fans, both of which are often necessary to provide desirable operations. Similarly, power supplies, transformers, and other device components produce noise. Circulating liquids, in fluid or gas form, also create noise. Component heating and cooling create noise, such as noise emitted when plastic and metal parts cool from high temperature. Accordingly, canceling noise after it is created is often important.

Passive noise cancellation includes sound absorbing materials. These are highly effective. However, for many reasons, there is an increased interest in active noise cancellation. An active noise cancellation system may be, in some instances, more efficient and less bulky than passive noise cancellation. There remains a need for an improved active noise cancellation.

Many systems that require noise control exhibit two types of disturbances: periodic and non-periodic. Recently, work in the area of repetitive control has produced good results in the rejection of periodic disturbances. Repetitive controllers can be viewed as an extension of the internal model principle. An internal model, often called a memory loop, is placed in the feedback loop in order to cancel the repetitive disturbance. Since the standard memory loop is marginally unstable, it is impractical to implement without modification. Typically, two filters are used to modify the memory loop. One filter is used to create a stable model, and one filter is used to eliminate high frequency components. This method results in a high order internal model that is designed on a trial and error basis. Additionally, non-periodic effects are often left out of the analysis, and the resulting controller can over amplify these components.

The invention is directed to methods and systems to address these needs.

DISCLOSURE OF INVENTION

One embodiment of the invention uses broadband feedforward sound compensation, which is a sound reduction technique where a sound disturbance is measured at an upstream location of the (noisy) sound propagation and cancelled at a downstream direction of the (noisy) sound propagation. An active noise control algorithm is the actual computation of a control signal (or compensation signal) that is able to reduce the effect of an undesired sound source by generating an out-of-phase sound source. To achieve proper sound cancellation, the active noise control algorithm must take into account the dynamic effects of the propagation of both the undesired and the out-of-phase sound source. The invention provides such a feedforward noise control algorithm and method that takes into account the dynamic effects of sound propagation.

The inventive active noise control algorithm described in this invention uses a FIR (Finite Impulse Response) filter where the orthogonal basis functions in the filter are chosen on the basis of the dynamics of the sound propagation. In this approach the standard tapped delay line of the FIR filter is replaced by a FIR filter that contains information on how the sound propagates though the system. The so-called generalized FIR (GFIR) filter has a much larger dynamic range while maintaining the linear parameter dependency found in a conventional FIR filter. As a result, adaptive and recursive estimation techniques can be used to estimate the parameters of the GFIR filter. The GFIR filter requires an initialization that contains knowledge on sound propagation dynamics. Once actuators and sensors for active noise control have been placed in the system, the data from the actuators and sensors can be used to measure and characterize the dynamics of the sound propagation, and this information is used to initialize the GFIR filter.

Another embodiment of the invention concerns a feedback sound compensation system that treats the effects of both the periodic and non-periodic noise components. With the present invention, we are able to design a sound control algorithm that emphasizes the elimination of periodic components without over amplifying the non-periodic sound components. The controller is tuned to reject the periodic disturbances until there is no appreciable difference between the periodic and non-periodic disturbances.

The periodic components are attenuated with the use of an internal model. Instead of starting with a standard memory loop and filtering, we directly create a stable internal model to shape the controller to reject specific deterministic disturbances. Using known $H_2$ control theory, we are able to incorporate periodic and non-periodic disturbances into the design. In this manner, we are able to design a low order controller that uses an internal model and a stochastic model to eliminate periodic disturbances in the presence of random noise.

A wide variety of devices and systems in various fields may benefit from the invention, e.g., forced air systems, electronic devices, computer systems, manufacturing systems, projectors, etc.

BRIEF DESCRIPTION OF DRAWINGS

FIG. 5 is a graph showing time data of a fan noise;

FIG. 6 is a graph showing the power spectral density of the fan noise shown in the graph of FIG. 5;

FIG. 7 is a block diagram showing a model for periodic and non-periodic noise disturbances.

BEST MODE FOR CARRYING OUT THE INVENTION

Figure 1:
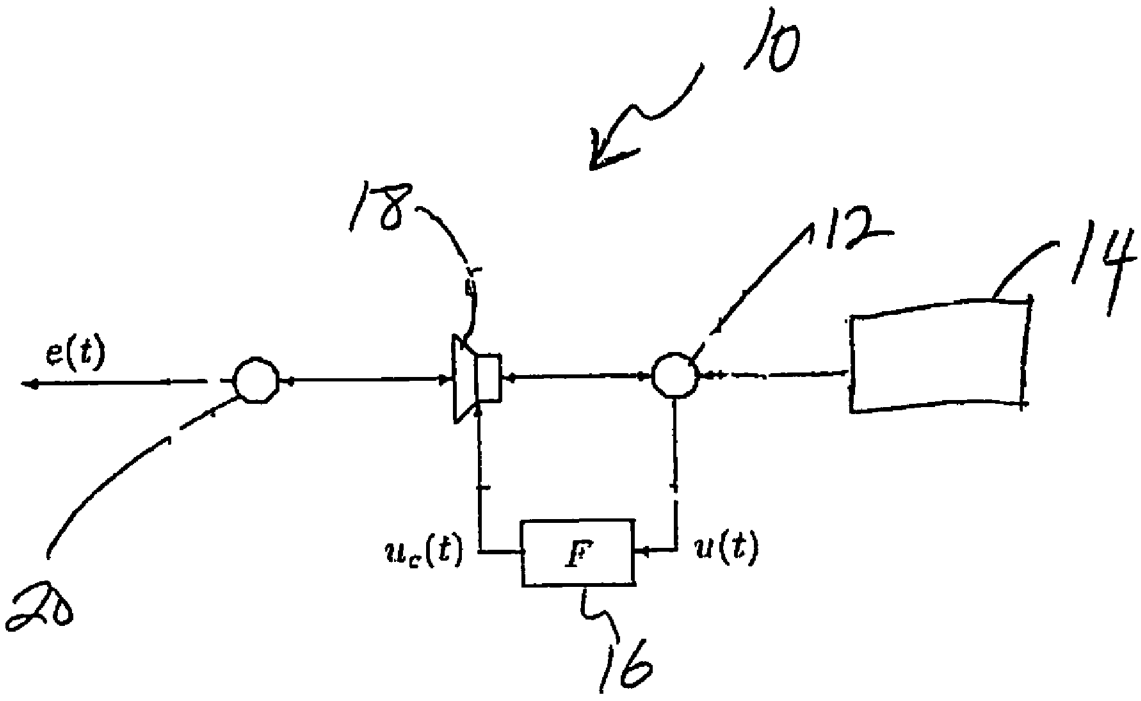
FIG. 1 is a schematic diagram of a feedforward active noise control (ANC) system in accordance with one embodiment of the present invention.

Turning now to FIG. 1, an active noise control (ANC) system 10 in accordance with one embodiment of the present invention includes an input microphone 12 for measuring noise from an external noise source 14, such as fan noise in a forced-air cooling system, for example. The (amplified) signal u(t) from the input microphone 12 is fed into a feedforward compensator (F) 16 that controls the signal $u_c(t)$ to a control speaker 18 for sound compensation. A signal e(t) from an error microphone 20 is used for evaluation of the effectiveness of the ANC system 10.

Figure 2:
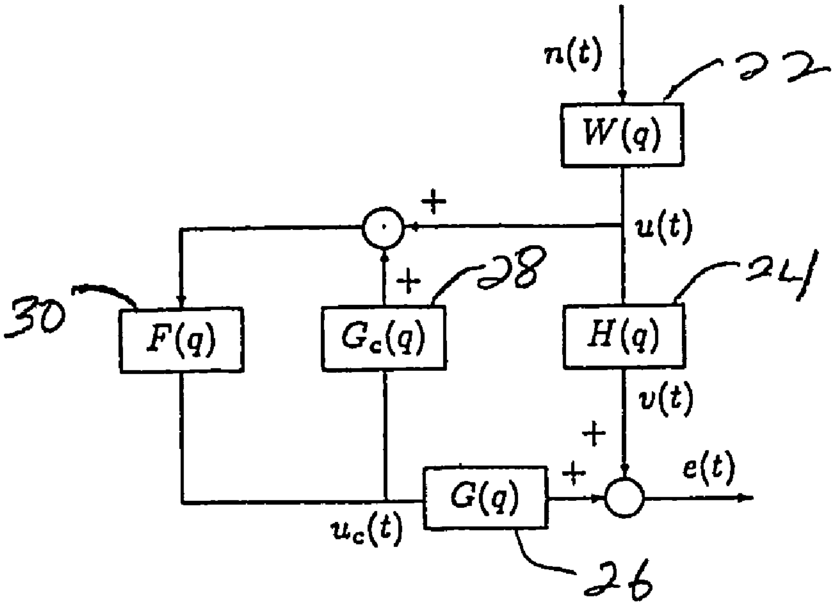
FIG. 2 is a block diagram showing a model of the ANC system of FIG. 1.

In order to analyze the design of the feedforward compensator 16, consider the block diagram depicted in FIG. 2. Following this block diagram, the dynamical relationships between signals in the ANC system 10 are characterized by discrete time transfer functions, with qu(t)=u(t+1) indicating a unit step time delay. The spectrum of noise disturbance u(t) at the input microphone 12 is characterized by filtered white noise signal n(t) where W(q) 22 is a (unknown) stable and stable invertible noise filter. The dynamic relationship between the input u(t) and the error e(t) microphone signals is characterized by H(q) 24 whereas G(q) 26 characterizes the relationship between control speaker signal and error e(t) microphone signal. Finally, $G_c(q)$ 28 is used to indicate the acoustic coupling from control speaker 18 signal back to the input u(t) microphone 12 signal that creates a positive feedback loop with the feedforward F(q). For the analysis, we assume in this that all transfer functions in FIG. 2 are stable and known. The error microphone signal e(t) can be described by $$e(t) = W(q)\left[H(q) + \frac{G(q)F(q)}{1 - G_c(q)F(q)}\right]n(t) \tag{1}$$

and is a stable transfer function if the positive feedback connection of F(q) 30 and $G_c(q)$ 28 is stable. When the transfer functions in FIG. 2 are known, perfect feedforward noise cancellation can be obtained in case $$F(q) = -\frac{H(q)}{G(q) - H(q)G_c(q)} \tag{2}$$

-continued $$= \frac{\tilde{F}(q)}{1 + \tilde{F}(q)G_c(q)},\ \tilde{F}(q) := -\frac{H(q)}{G(q)}$$

and can be implemented as a feedforward compensator 16 in case F(q) 30 is a stable and causal transfer function. The expression in equation (2) can be simplified for the situation where the effect of acoustic coupling $G_c$ can be neglected. In that case, the feedforward compensator 16 can be approximated by $$F(q) \approx \tilde{F}(q) = -\frac{H(q)}{G(q)} \tag{3}$$

and for implementation purposes it would be required that F(q) 30 be a causal and stable filter. In general, the filter F(q) 30 in equation (2) or (3) is not a causal or stable filter due to the dynamics of G(q) 26 and H(q) 24 that dictate the solution of the feedforward compensator. Therefore, an optimal approximation has to be made to find the best causal and stable feedforward compensator. With equation (1) the variance of the discrete time error signal e(t) is given by $$\frac{\lambda}{2\pi}\int_{-\pi}^{\pi}|W(e^{j\omega})|^2\left|H(e^{j\omega}) + \frac{G(e^{j\omega})F(e^{j\omega})}{1 - G_c(e^{j\omega})F(e^{j\omega})}\right|^2 d\omega$$

where λ denotes the variance of n(t). In case variance minimization of the error microphone signal e(t) is required for ANC, the optimal feedforward controller (F) 16 is found by the minimization $$\min_\theta \int_{\omega=-\pi}^{\omega=\pi} |L(e^{j\omega}, \theta)|^2\, d\omega := \min_\theta \|L(q, \theta\|_2, \tag{4}$$
$$L(q, \theta) = W(q)\left[H(q) + \frac{G(q)F(q, \theta)}{1 - G_c(q)F(q, \theta)}\right]$$

where the parametrized filter F(q,θ) is required to be a causal and stable filter, in which θ is a real valued parameter determined by the minimization in equation (4).

The minimization in equation (4) can be simplified to $$\min_\theta \int_{\omega=-\pi}^{\omega=\pi} |L(e^{j\omega}, \theta)|^2\, d\omega := \min_\theta \|L(q, \theta\|_2,$$
$$L(q, \theta) = W(q)[H(q) + G(q)F(q, \theta)]$$

in case the effect of acoustic coupling $G_c$ can be neglected. The minimization in equation (4) is a standard 2-norm based feedback control and model matching problem that can be solved in case the dynamics of W(q) 22, G(q) 26, H(q) 24 and $G_c(q)$ 28 are known.

In case the transfer functions H(q) 24, G(q) 26 and $G_c(q)$ 28 are predetermined, but possibly unknown. It is important to make a distinction between varying dynamics and fixed dynamics in the ANC system 10 for estimation and adaptation purposes. An off-line identification technique can be used to estimate these transfer functions to determine the essential dynamics of the feedforward controller. Subsequently, the spectral contents of the sound disturbance characterized by the (unknown) stable and stably invertible filter W(q) 22 is the only varying component for which adaptation of the feedforward control is required. Instead of separately estimating the unknown transfer functions and computing the feedforward controller via an adaptive optimization of equation (4), a direct estimation of the feedforward compensator 16 can also be performed.

For the analysis of the direct estimation of the feedforward compensator 16 we assume that the acoustic coupling $G_c$ can be neglected to simplify the formulae. In that case, the error signal e(t) is given by $$e(t,\theta)=H(q)u(t)+F(q,\theta)G(q)u(t) \tag{5}$$

and definition of the signals $$y(t):=H(q)u(t), u_f(t):=-G(q)u(t) \tag{6}$$

leads to $$e(t,\theta)=y(t)-F(q,\theta)u_f(t)$$

for which the minimization $$\min_\theta \frac{1}{N}\sum_{t=1}^{N} e(t,\theta) \tag{7}$$

to compute the optimal feedforward filter F(q;θ) is a standard output error (OE) minimization problem in a prediction error framework. Using the fact that the input signal u(t) satisfies $\|u\|_2=|W(q)|^2\lambda$, the minimization of equation (7) for $\lim_{N\to\infty}$ can be rewritten into the frequency domain expression $$\min_\theta \int_{-\pi}^{\pi} |W(e^{j\omega})|^2 |H(e^{j\omega}) + G(e^{j\omega})F(e^{j\omega},\theta)|^2 \, d\omega \tag{8}$$

using Parceval's theorem. Due to the equivalency of equations (8) and (4), the same 2-norm objectives for the computation of the optimal feedforward compensator are used.

It should be noted that the signals in equation (6) may be obtained by performing a series of two experiments. The first experiment is done without a feedforward compensator 16, making e(t)=H(q)u(t), $\triangleq$ y(t), and e(t) is the signal measured at the error microphone 20. The input signal $u_f(t)$ can be obtained by applying the measured input microphone signal u(t) from this experiment to the control speaker 18 in a second experiment that is done without a sound disturbance. In that situation $e(t)=G(q)u(t)\triangleq-u_f(t)$.

In general, the OE minimization of equation (7) is a non-linear optimization but reduces to a convex optimization problem in case F(q, θ) is linear in the parameter θ. Linearity in the parameter θ is also favorable for on-line recursive estimation of the filter and may be achieved by using a FIR filter parametrization $$F(q,\theta)=\theta_0+\sum_{k=1}^{N}\theta_k q^{-k},\ \theta=[\theta_0,\theta_1,\ldots,\theta_N] \tag{9}$$

for the feedforward compensator F(q,θ). A FIR filter parametrization also guarantees the causality and stability of the feedforward compensator 16 for implementation purposes.

To improve the approximation properties of the feedforward compensator 16 in the ANC system 10, the linear combination of tapped delay functions $q^{-1}$ in the FIR filter of (9) are generalized to $$F(q,\theta)=\theta_0+\sum_{k=1}^{N}\theta_k f_k(q),\ \theta=[\theta_0,\theta_1,\ldots,\theta_N] \tag{10}$$

where $f_k(q)$ are generalized (orthonormal) basis functions that may contain knowledge on system dynamics, $\theta_0$ is the direct feedthrough term of the generalized FIR filter and $\theta_k$ are the optimal filter coefficients of said generalized FIR filter, as described in P. S. C. Heuberger, P. M. J. Van Den Hof, and O. H. Bosgra, "A generalized orthonormal basis for linear dynamical systems," *IEEE Transactions on Automatic Control*, vol. 40(3), pp. 451-465, 1995, which is incorporated herein by reference.

Figure 3:
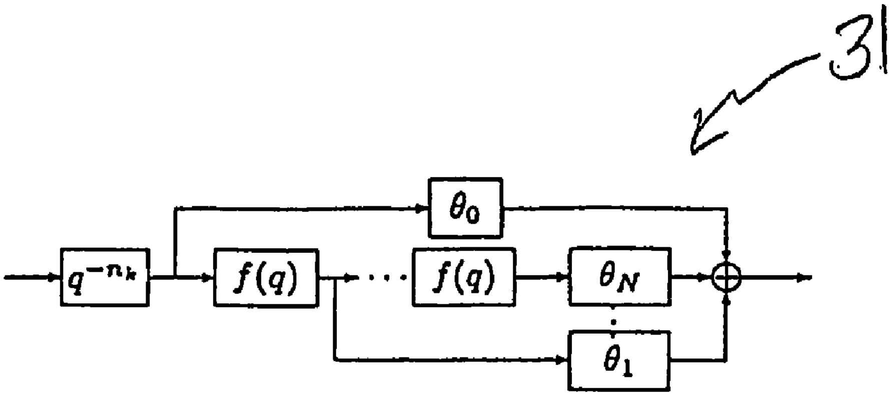
FIG. 3 is a block diagram of a generalized FIR filter derived from the model of FIG. 2.

The generalized FIR filter can be augmented with standard delay functions $$F(q)=q^{-nk}\left[\theta_0+\sum_{k=1}^{N}\theta_k f_k(q)\right],\ \theta=[\theta_0,\theta_1,\ldots,\theta_N] \tag{11}$$

to incorporate a delay time of $n_k$ time steps in the feedforward compensator. A block diagram of the generalized FIR filter F(q) 31 in equation (11) is depicted in FIG. 3. It can be seen that it exhibits the same tapped delay line structure found in a conventional FIR filter, with the difference of more general basis functions $f_k(q)$. In the generalized FIR filter 31 knowledge of the (desired) dynamical behavior can be incorporated in the basis function $f_k(q)$. Without any knowledge of desired dynamic behavior, the trivial choice of $f_k(q)=q^{-1}$ reduces the generalized FIR filter 31 to the conventional FIR filter. If a more elaborate choice for the basis function $f_k(q)$ is incorporated, then equation (11) can exhibit better approximation properties for a much smaller number of parameters N than used in a conventional FIR filter 31. Consequently, the accuracy of the optimal feedforward controller will substantially increase.

Continuing the line of reasoning described above, where the effect of the acoustic coupling $G_c(q)$ 28 (shown in FIG. 2) is assumed to be negligible, the parametrization of the generalized FIR filter 31 in equation (11) will be used in the OE minimization of equation (7). As the generalized FIR filter 31 is linear in the parameters, convexity of the OE minimization is maintained and on-line recursive estimation techniques can be used to estimate and adapt the feedforward controller 16 for ANC purposes. For the construction of the feedforward controller 16 based on the generalized FIR filter F(q) 31, we make a distinction between an initialization step and the recursive estimation of the generalized FIR filter 31.

To initialize the on-line adaptation of the generalized FIR filter 31, the signals y(t) and $u_f(t)$ in equation (6) have to be available to perform the OE-minimization. With no feedforward controller in place, the signal y(t) is readily available via $$y(t)=H(q)u(t)=e(t) \tag{12}$$

Because G(q) 26 is fixed once the mechanical and geometrical properties of the ANC system in FIG. 2 are fixed, an initial off-line estimation can be used to estimate a model for G(q) 26 to construct the filtered input signal $u_f(t)$.

Estimation of a model of G(q), indicated by $\hat{G}(q)$, can be done by performing an experiment using the control speaker signal $u_c(t)$ (see FIG. 1) as excitation signal and the error microphone signal e(t) as output signal. Construction of the prediction error $$\epsilon(t,\beta)=e(t)-G(q,\beta)u_c(t)$$

and a minimization $$\hat{G}(q) := G\left(q, \hat{\beta}\right), \hat{\beta} = \underset{\beta}{\operatorname{argmin}}\frac{1}{N}\sum_{t=0}^{N}\varepsilon^2(t, \beta) \tag{13}$$

yields a model $\hat{G}(q)$ for filtering purposes. Since $\hat{G}(q)$ is used for filtering purposes only, a high order model can be estimated to provide an accurate reconstruction of the filtered input signal via $$\hat{u}_f(t):=\hat{G}(q)u(t) \tag{14}$$

where $\hat{u}_f(t)$ is a filter version, or model, of the control signal $u_f(t)$.

To facilitate the use of the generalized FIR filter 31, a choice is made for the basis functions $f_k(q)$ in equation (10). A low order model for the basis function will suffice, as the generalized FIR model 31 will be expanded on the basis of $f_k(q)$ to improve the accuracy of the feedforward compensator 16. As part of the initialization of the feedforward compensator 16, a low order IIR model $\hat{F}(q)$ in equation (10) of the feedforward filter F(q) 31 can be estimated with the initial signals available from (12), (14) and the OE-minimization $$\hat{F}(q) := F\left(q, \hat{\theta}\right), \hat{\theta} = \underset{\theta}{\operatorname{argmin}}\frac{1}{N}\sum_{t=0}^{N}\varepsilon^2(t, \theta) \tag{15}$$

of the prediction error $$\epsilon(t,\theta)=y(t)-F(q,\theta)\hat{u}_f(t)$$

where $\hat{u}_f(t)$ is given in equation (14). An input balanced state space realization of the low order model $\hat{F}(q)$ is used to construct the basis functions $f_k(q)$ in equation (10).

With a known feedforward $F(q,\theta_{k-1})$ already in place, the signal y(t) can be generated via $$y(t)=H(q)u(t)=e(t)+F(q,\theta_{k-1})u_f(t) \tag{16}$$

and requires measurement of the error microphone signal e(t), and the filtered input signal $u_f(t)=G(q)u(t)$ that can be simulated by equation (14). With the signal y(t) in equation (16), $\hat{u}_f(t)$ in equation (14) and the basis function $f(q)$ in equation (10) found by the initialization in equation (15), a recursive minimization of the feedforward filter is done via a standard recursive least squares minimization $$\theta_k = \underset{\theta}{\operatorname{argmin}}\frac{1}{k}\sum_{t=0}^{k}\lambda(t)[y(t) - F(q, \theta)\hat{u}_f(t)]^2 \tag{17}$$

where F(q, θ) is parametrized according to equation (11) and λ(t) indicates an exponential forgetting factor on the data. As the feedforward compensator or controller 16 is based on the generalized FIR model 31, the input $\hat{u}_f(t)$ is also filtered by the tapped delay line of basis functions. Since the filter is linear in the parameters, recursive computational techniques can be used to update the parameter $\theta_k$.

In the implementation of feedforward based active noise control (ANC) system 10, design freedom for the location of the input microphone 12 should be exploited to enhance the performance of the ANC system. The performance can be improved by 1: minimize coupling between control speaker 18 and input microphone 12, also known as acoustic coupling and 2: maximize the effect of the feedforward filter 16 for active noise control.

In order to study these two effects on the performance of the ANC system 10, consider a certain location of the input microphone in the ANC system 10. For that specific location, the transfer functions H(q), G(q) in equation (3) are fixed, but unknown. As a result, the performance of the ANC system 10 solely depends on the design freedom in the feedforward compensator F(q, θ) 31 to minimize the error signal e(t, θ) in equation (5). The ability to minimize the error signal e(t, θ) is restricted by the parametrization of F(q, θ) and an optimization of the feedforward filter F(q, θ) can be performed by considering the parametrized error signal e(t, θ) in terms of the signals $y(t):=H(q)u(t), u_f(t):=-G(q)u(t)$ in equation (6). For a specific location of the input microphone 12, the signals in (6) are easily obtained by performing a series of two experiments. The two experiments measure the input and error microphone signals u(t) and e(t).

The first experiment is done without feedforward compensation. Hence F(q, θ)=0 and the error microphone signal satisfies $$e_1(t)=H(q)u(t) \tag{18}$$

In addition, the input microphone 12.

$$\tilde{u}(t)=u(t)+v(t) \tag{19}$$

is measured, where v(t) indicates possible measurement noise on the input microphone signal u(t). This results in additional disturbances on the input microphone signal u(t) that need to be considered in the optimal location of the microphone 12.

The second experiment is done with the noise source 14 turned off, eliminating the presence of the external sound disturbance. Subsequently, the measured input microphone signal $-\tilde{u}(t)$ given in equation (19) from the first experiment is applied to the control speaker 18, yielding the error microphone signal $$e_2(t)=-G(q)\tilde{u}(t)=-G(q)u(t)-G(q)v(t) \tag{20}$$

With $u_f(t):=-G(q)u(t)$, the error microphone signal e(t, θ) can be written as $$e(t,\theta)=e_1(t)-F(q,\theta)e_2(t)-F(q,\theta)G(q)v(t) \tag{21}$$

Alternatively, both experiments can be combined by using a filtered input signal $u_f(t)$ that is based on an estimated model $\hat{G}(q)$ of G(q). Because G(q) is fixed once the location of the control speaker 18 is determined, an initial off-line estimation can be used to estimate a model for G(q) to construct the filtered input signal $u_f(t)$.

In the absence of the noise v(t) on the input microphone 12, the minimization of e(θ) in (21) is equivalent to the minimization of e(t, θ) in (6). As a result, the obtainable performance of the ANC 10 system for a specific location of the input microphone 12 can be evaluated directly on the basis of the error microphone signals $e_1(t)$ and $e_2(t)$ as defined in equation (18) and (20) and obtained from the first and second experiment as defined above. The result is summarized in the following proposition.

Proposition 1. The performance of the feedforward ANC system 10 for a specific location of the input microphone 12 is characterized by $v_N(\hat{\theta})$. The numerical value of $v_N(\hat{\theta})$ is found by measuring $e_1(t)$ and $e_2(t)$ for t=1, . . . , N as described by the experiments above, and solving an OE model estimation problem $$\hat{\theta} = \underset{\theta \in R^d}{\operatorname{argmin}} V_N(\theta), \text{ with}$$

$$V_N(\theta) := \frac{1}{N}\sum_{t=1}^{N} \varepsilon^2(t, \theta)$$

$$\varepsilon(t, \theta) := e_1(t) - F(q, \theta)e_2(t)$$

for a finite size d parameter $\theta \in R^d$ that represents the coefficients of a finite order filter F(q, θ).

A finite number d of filter coefficients is chosen in Proposition 1 to provide a feasible optimization of the filter coefficients. It should be noted that an FIR parametrization $$F(q, \theta) = \theta_0 + \sum_{k=1}^{d} \theta_k q^{-k}, \ \theta = [\theta_0, \theta_1, \dots, \theta_d]$$

leads to an affine optimization of the filter coefficients. Although FIR filter representations (i.e., equation (9)) require many filter coefficients $\theta_k$ for an accurate design of a feedforward filter, the FIR filter is used only to evaluate the possible performance of the ANC system 10 for a specific input microphone 12 location. For the actual ANC system 10 the feedforward filter is replaced by the generalized FIR filter as presented above.

In accordance with another embodiment of the present invention, an active noise control (ANC) system includes a feedback system that treats the affects of both the periodic and non-periodic noise disturbances. With the present system we are able to design a controller that emphasizes the elimination of periodic components without over amplifying the non-periodic components using an additional feedback control algorithm. The controller is tuned to reject the periodic disturbances until there is no appreciable difference between the periodic and non-periodic disturbances.

Figure 4:
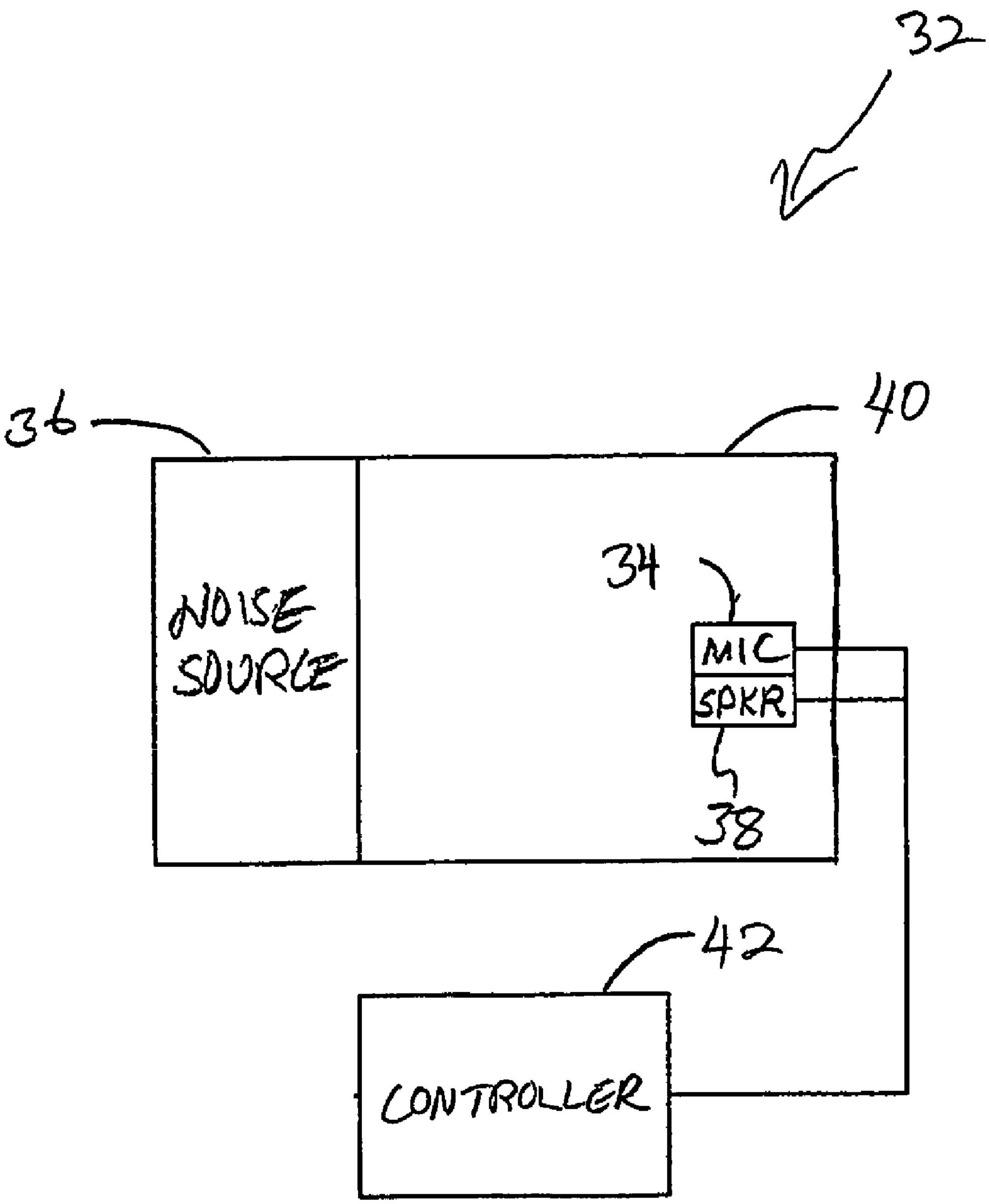
FIG. 4 is a schematic diagram of a feedback active noise control (ANC) system in accordance with one embodiment of the present invention.

Turning to FIG. 4, a feedback ANC system 32 in accordance with one embodiments includes a microphone 34 for measuring noise from a noise source 36, such as, for example, a server cooling fan; a speaker 38 for generating appropriate signal to cancel unwanted periodic noise from the noise source 36; and a mount 40 for holding the microphone 34 and the speaker 38 proximate the noise source 36. A controller 42 is provided for controlling the output of the speaker 38 based on the noise measured by the microphone 34.

The speaker 38 and the microphone 34 are positioned inside of the mount 40, which may be a polyurethane acoustical foam and acrylic, and is orientated so that the sound from the noise source 36 propagates towards the microphone 34. It should be noted that the speaker 38 and the microphone 34 are very close together and are mounted proximate to and downstream of the noise source 36.

The noise due to the noise source 36 such as, for example, a server cooling fan, as measured by the microphone 34, is shown in FIGS. 5 and 6. FIG. 5 shows the time data of the fan noise, and FIG. 6 shows the power spectral density. There are two distinct types of disturbances. One is periodic; the peaks at evenly spaced frequencies are harmonics of the fan (approximately every 1000 Hz, for example). The other is non-periodic noise due to turbulence, vibrations, and the actual non-periodic noise of the fan. The effect of wind and vibrations can be modeled as filtered white noise in the measurement.

The design method for the active noise feedback control algorithm for the controller 42 in accordance with an embodiment of the invention divides the source noise into two distinct disturbances: periodic and non-periodic. The present method helps lower the order of the controller 42 and simplifies the disturbance modeling. FIG. 7 shows how both disturbances are modeled, where $H_n(q)$ 44 is the non-periodic disturbance model, $H_p(q)$ 46 is the periodic disturbance model, and G(q) 48 is the dynamic feedback relation between feedback control speaker 38 and feedback control microphone 34 and defined as "the plant" in the following. In FIG. 7 the signal u(t) is the signal send to the feedback control speaker 38 and y(t) is the signal measured by the feedback control microphone 34. The signal $v_n(t)$ models the non-periodic noise component of the sound as a filtered white noise signal e(t) and $v_p(t)$ models the periodic noise component of the sound.

The non-periodic or random disturbances are modeled as colored noise. That is, $v_n(t)$ is a random process that is driven by white noise e(t) that is filtered by $H_n(q)$ 44, where q is the time shift operator. The periodic disturbances are modeled as a standard memory loop $H_p(q)$ 46 with an unknown initial condition $x_0$. When added together, $v_n(t)$ and $v_p(t)$ produce the same result as a single disturbance model.

Figure 8:
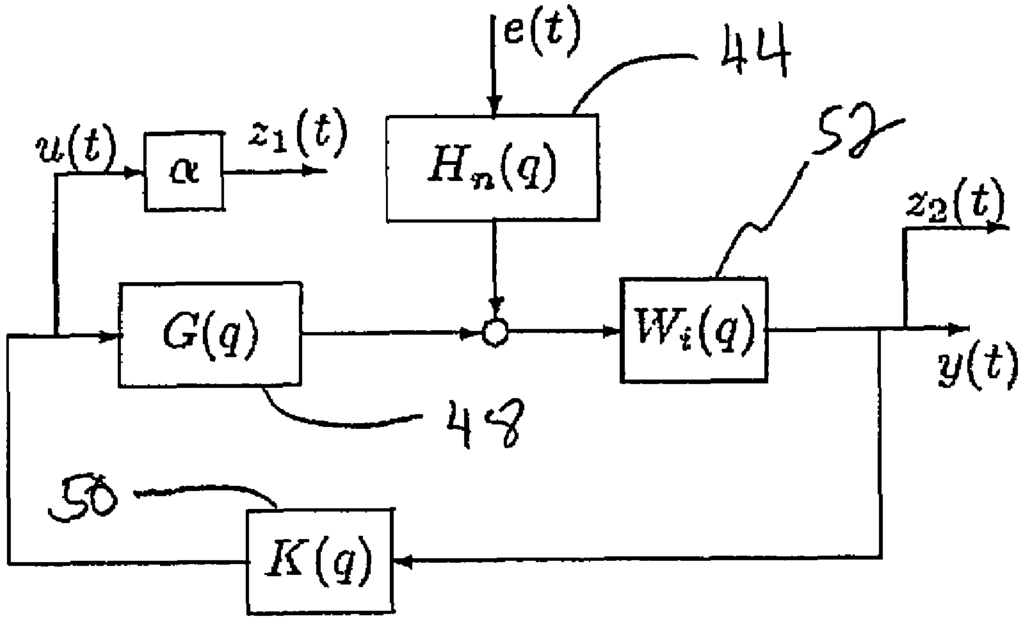
FIG. 8 is a block diagram showing a model for a controller shown in the feedback ANC system of FIG. 7.

In one embodiment of the invention, the disturbance model shown in FIG. 7 is modified, as shown in FIG. 8, to design the optimal control algorithm for the reduction of periodic noise disturbances. The signal $z_1(t)$ and $z_2(t)$ are used to measure the performance of the feedback ANC 32 system, where α can be used to specify the relative weighting between the performance signals $z_1(t)$ and $z_2(t)$. The optimal control algorithm K(q) 50 minimizes the $H_2$ norm of the transfer function matrix between e(t) and ($z_1(t)$ $z_2(t)$). The signals e(t) and ($z_1(t)$ $z_2(t)$) are chosen so that the control energy and output will be minimized by the optimal feedback control algorithm K(q) 50. To account for the periodic disturbances that need to be cancelled, an internal model representation $W_i(q)$ 52 is placed in the path from e(t) to y(t) so that the resulting controller will have the general shape of the internal model. Substantially perfect cancellation of all periodic noise components could be achieved by choosing $W_i(q)=H_p(q)$ (shown in FIG. 8) but the presence of such an internal model in the feedback control algorithm may cause instabilities of the feedback ANC system 32. The main purpose of $W_i(q)$ 52 is to model only those period components in the noise filter $H_p(q)$ 46 for which periodic noise disturbance rejection is desired. This makes the control algorithm less complex and stability of the feedback ANC system 32 can be satisfied much easier. Subsequently, the optimal design of the feedback control algorithm is solved by solving the minimization:

$$K(q) = \underset{K}{\operatorname{argmin}} \left\| \begin{matrix} \dfrac{\alpha W_i(q)K(q)H_n(q)}{1 - G(q)W_i(q)K(q)} \\ \dfrac{W_i(q)H_n(q)}{1 - G(q)W_i(q)K(q)} \end{matrix} \right\|_2 \quad (22)$$

In the minimization of equation (22), a feedback control algorithm is computed that will not invert the effect of the internal model $W_i$(q) 52. As a result, the combined active noise feedback control algorithm K(q)$W_i$(q) will have the general shape of $W_i$(q) and eliminate the periodic disturbances in the noise components.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. An active noise control apparatus for reducing noise from a noise source, comprising:

a first detector for detecting noise produced by the noise source;

a generalized finite impulse response (FIR) filter for receiving noise signals of the detected noise from said first detector, and generating control signals for reducing the noise from the noise source; and a sound generator for producing sound based on said control signals from said generalized FIR filter for substantially canceling the noise from the noise source;

wherein said generalized FIR filter is described by $$F(q, \theta) = \theta_0 + \sum_{k=1}^{N} \theta_k f_k(q),\ \theta = [\theta_0, \theta_1, \ldots, \theta_N]$$

where $f_k$(q) are generalized (orthonormal) basis functions including information on a desired dynamic behavior of said generalized FIR filter, $\theta_0$ is the direct feedthrough term of said generalized FIR filter and $\theta_k$ are optimal filter coefficients of said generalized FIR filter;

wherein said generalized FIR filter is constructed by initializing said basis function $f_k$(q), and recursively estimating said $\theta_k$ based on said initialized basis function $f_k$(q); and wherein said basis function $f_k$(q) are initialized by a predetermined dynamical model that includes initial approximate information dynamics of said generalized FIR filter.

2. An active noise control apparatus for reducing noise from a noise source, comprising:

a first detector for detecting noise produced by the noise source;

a generalized finite impulse response (FIR) filter for receiving noise signals of the detected noise from said first detector, and generating control signals for reducing the noise from the noise source;

a sound generator for producing sound based on said control signals from said generalized FIR filter for substantially canceling the noise from the noise source; and a second detector for detecting noise downstream of said sound generator;

wherein a signal of the noise detected by the second detector is described by $$e(t) = W(q)\left[H(q) + \frac{G(q)F(q)}{1 - G_c(q)F(q)}\right]n(t)$$

where, W(q) is a stable and stable invertible noise filter for a white noise signal n(t); H(q) characterizes a dynamic relationship between the input signal u(t) from said first detector and said signal e(t) detected by said second detector; G(q) characterizes the relationship between said control signal from said generalized FIR filter F(q) and said signal e(t) detected by said second detector; and $G_c$(q) indicates an acoustic coupling from said sound generator signal back to said signal u(t)from said first detector that creates a positive feedback loop with said generalized FIR filter F(q).

3. The apparatus as defined in claim 2, wherein said first detector is located based on conditions at the second detector which satisfy $e_1(t)=H(q)u(t)$ and $e_2(t)=-G(q)\tilde{u}(t)=-G(q)u(t)-G(q)v(t)$ where v(t) indicates a disturbance detected by said first detector.

4. A method for reducing noise from a noise source in an active noise control system, comprising:

detecting first noise produced by the noise source;

generating control signals from a generalized finite impulse response (FIR) filter for reducing the first noise from the noise source based on a first signal of said detected noise; and producing sound based on said control signals for substantially canceling said first noise from the noise source;

wherein said generalized FIR filter is described by $$F(q, \theta) = \theta_0 + \sum_{k=1}^{N} \theta_k f_k(q),\ \theta = [\theta_0, \theta_1, \ldots, \theta_N]$$

where $f_k$(q) are generalized (orthonormal) basis functions containing information on a desired dynamic behavior of said generalized FIR filter, $\theta_0$ is a direct feedthrough term of said generalized FIR filter and $\theta_k$ are optimal filter coefficients of said generalized FIR filter;

wherein said generalized FIR filter is constructed by initializing said basis function $f_k$(q), and recursively estimating said $\theta_k$ based on said initialized basis function $f_k$(q); and wherein said basis function $f_k$(q) is initialized by a predetermined dynamical model tat includes initial approximate information dynamics of said generalized FIR filter.

5. A method for reducing noise from a noise source in an active noise control system, comprising:

detecting first noise produced by the noise source;

generating control signals from a generalized finite impulse response (FIR) filter for reducing the first noise from the noise source based on a first signal of said detected noise;

producing sound based on said control signals for substantially canceling said first noise from the noise source; and detecting second noise after said sound based on said control signals has been produced by a second detector;

wherein a second signal of the second noise detected after said sound based on said control signals has been produced by the second detector is described by $$e(t) = W(q)\left[H(q) + \frac{G(q)F(q)}{1 - G_c(q)F(q)}\right]n(t)$$

where, W(q) is a stable and stable invertible noise filter for a white noise signal n(t); H(q) characterizes a dynamic relationship between the first signal u(t) and said second signal e(t); G(q) characterizes the relationship between said control signal from said generalized FIR filter F(q) and said first signal e(t); and $G_c(q)$ indicates an acoustic coupling from said sound generator signal back to said first signal u(t) that creates a positive feedback loop with said generalized FIR filter F(q).

6. The method as defined in claim 5, wherein said first noise is detected at a location based on conditions which satisfy $$e_1(t)=H(q)u(t) \text{ and}$$

$$e_2(t)=-G(q)\tilde{u}(t)=-G(q)u(t)-G(q)v(t)$$

where v(t) indicates a third noise detected along with said first noise.

7. An active noise control apparatus for reducing periodic noise from a noise source, comprising:

a detector for detecting noise produced by the noise source;

a controller for generating control signals for compensating the periodic noise detected in the noise; and a sound generator for producing sound based on said control signals from said controller for substantially canceling the periodic noise from the noise source;

wherein said control signal is generated based on an equation, $$K(q) = \underset{K}{\operatorname{argmin}} \left\| \begin{matrix} \dfrac{\alpha W_i(q)K(q)H_n(q)}{1 - G(q)W_i(q)K(q)} \\ \dfrac{W_i(q)H_n(q)}{1 - G(q)W_i(q)K(q)} \end{matrix} \right\|_2$$

where, $W_i(q)$ is a discrete time internal dynamical model for reducing periodic disturbances, $H_n(q)$ is a discrete time filter used to model the spectrum of the non-periodic noise disturbances, G(q) is a discrete time filter that models the dynamics between sound generator and said detector and α is a scalar real-valued constant.

8. The apparatus as defined in claim 7, wherein said controller comprises a feedback controller.

9. The apparatus as defined in claim 7, wherein said detector is a microphone and said sound generator is a speaker, said microphone and said speaker being positioned proximate and downstream of the noise source.

10. A method for reducing periodic noise from a noise source, comprising:

detecting noise produced by me noise source;

generating control signals from a controller for compensating the periodic noise detected in the noise; and producing sound based on said control signals from said controller for substantially canceling the periodic noise from the noise source;

wherein said control signal is generated based on an equation, $$K(q) = \underset{K}{\operatorname{argmin}} \left\| \begin{matrix} \dfrac{\alpha W_i(q)K(q)H_n(q)}{1 - G(q)W_i(q)K(q)} \\ \dfrac{W_i(q)H_n(q)}{1 - G(q)W_i(q)K(q)} \end{matrix} \right\|_2$$

where, $W_i(q)$ is a discrete time internal dynamical model for reducing periodic disturbances, $H_n(q)$ is a discrete time filter used to model a spectrum of the non-periodic noise disturbances, G(q) is a discrete time filter that models the dynamics between a sound generator for producing said sound based on said control signals and a detector for detecting the noise produced by the noise source, and α is a scalar real-valued constant.

11. The method as defined in claim 10, wherein said controller comprises a feedback controller.

12. The method as defined in claim 10, wherein the noise is detected by a microphone and said sound based on said control signals from said controller is produced by a speaker, said microphone and said speaker being positioned proximate and downstream of the noise source.

* * * * *

UNITED STATES PATENT AND TRADEMARK OFFICE

CERTIFICATE OF CORRECTION

PATENT NO. : 7,688,984 B2
APPLICATION NO. : 10/579520
DATED : March 30, 2010
INVENTOR(S) : De Callafon It is certified that error appears in the above-identified patent and that said Letters Patent is hereby corrected as shown below:

In the Specification:

Col. 4, line 42 — Delete a portion of the equation as follows:

" $= \min_\theta \| L(q,\theta \|_2,$ "

and insert the following in its place:

-- $= \min\limits_{\theta} \| L(q,\theta) \|_2,$ --.

Col. 4, line 55 — Delete a portion of the equation as follows:

" $= \min_\theta \| L(q,\theta \|_2,$ "

and insert the following in its place:

-- $= \min\limits_{\theta} \| L(q,\theta) \|_2,$ --.

In the Claims:

Col. 12, line 65
Claim 4 — Delete "tat" and insert --that-- in its place.

Signed and Sealed this

Twenty-second Day of June, 2010

David J. Kappos
*Director of the United States Patent and Trademark Office*